United States Patent [19]

Barnes

[11] 4,364,907
[45] Dec. 21, 1982

[54] PROCESS FOR RECOVERY OF RHODIUM VALUES

[75] Inventor: Robert L. Barnes, Kingsport, Tenn.

[73] Assignee: Eastman Kodak Company, Rochester, N.Y.

[21] Appl. No.: 381,275

[22] Filed: May 24, 1982

Related U.S. Application Data

[63] Continuation-in-part of Ser. No. 274,859, Jun. 18, 1981, abandoned.

[51] Int. Cl.$^3$ .............................................. C01G 55/00
[52] U.S. Cl. ...................................... 423/22; 252/412; 252/414; 260/546; 260/549
[58] Field of Search ............... 252/412, 413, 414, 415, 252/420; 260/546, 549; 562/607, 608; 423/22

[56] References Cited

U.S. PATENT DOCUMENTS

| | | | |
|---|---|---|---|
| 3,887,489 | 6/1975 | Fannin et al. | 252/413 |
| 3,927,078 | 12/1975 | Leppole et al. | 260/549 |
| 4,046,807 | 9/1977 | Kuckertz | 260/549 |
| 4,188,363 | 2/1980 | Fell et al. | 423/22 |
| 4,234,719 | 11/1980 | Wan | 562/607 |
| 4,292,196 | 9/1981 | Homeier et al. | 252/412 |
| 4,329,521 | 5/1982 | Homeier | 252/412 |
| 4,340,569 | 7/1982 | Davidson | 423/22 |
| 4,340,570 | 7/1982 | Davidson | 423/22 |
| 4,341,741 | 7/1982 | Davidson | 423/22 |

FOREIGN PATENT DOCUMENTS 8002809 12/1980 U.S.S.R. .............................. 252/416

*Primary Examiner*—Herbert T. Carter
*Attorney, Agent, or Firm*—J. Frederick Thomsen; Daniel B. Reece, III

[57] ABSTRACT

Disclosed is a process for the recovery of residual rhodium from tar obtained by submitting a rhodium-containing catalyst-tar solution to an extraction using methyl iodide and aqueous hydrogen iodide, thereby recovering catalyst values in the aqueous phase and tar containing residual rhodium in the methyl iodide phase. The residual rhodium-containing tar is submitted to an extraction using a water-immiscible, inert solvent for the tar and aqueous ammonia to obtain residual rhodium in the aqueous phase. The catalyst-tar solution employed is derived from a production system in which acetic anhydride is prepared by carbonylating methyl acetate in the presence of rhodium, lithium and methyl iodide.

1 Claim, No Drawings

PROCESS FOR RECOVERY OF RHODIUM VALUES

This application is a continuation-in-part of Ser. No. 274,859, filed June 18, 1981 and now abandoned.

DESCRIPTION

This invention relates to a novel process for recovering rhodium catalysts values and, more particularly, to a method for recovering rhodium values from "tars" formed during the preparation of acetic anhydride by the rhodium-catalyzed carbonylation of methyl acetate.

The use of catalyst systems comprising rhodium and an iodine compound in the preparation of acetic anhydride by the carbonylation of methyl acetate has been reported in the patent literature. See, for example, Belgian Pat. No. 819,455, British Published patent application Ser. No. 2,013,184, Japanese Published patent applications Ser. Nos. 75-47921 and 75-47922 and U.S. Pat. Nos. 3,927,078 and 4,046,807. Those publications also disclose that the reaction rate can be increased if the catalyst system contains a promoter such as certain amines, phosphines and inorganic materials such as lithium compounds. The use of amines and phosphines, particularly under conditions giving high space-time yields, causes formation of tars which cannot be handled in a continuous process. The use of lithium compounds, such as lithium iodide or lithium acetate, does not entirely avoid the formation of tar but the tar that is formed is not unmanageable.

Tar formation, which is essentially unavoidable in the carbonylation of methyl acetate, increases as reaction conditions, such as temperature and pressure, are increased to obtain a desirably high space-time yield such as 400 g./l.-hr. or greater. It is known (U.S. Pat. No. 4,046,807) that the inclusion of hydrogen in the gas feed to the carbonylation reactor in a system employing triphenylphosphine can suppress tar formation. If not removed from the reaction system, tar will increase to the point where catalyst activity is greatly diminished which can eventually result in the termination of the carbonylation reaction.

Because of the cost of rhodium, high-efficiency catalyst recycling in the rhodium-catalyzed carbonylation of methyl acetate is of extreme importance for the successful operation of an acetic anhydride process. A survey of the literature on recovery/recycling procedures for rhodium species from reaction mixtures reveals a variety of methods relying on selective reduction and deposition of rhodium metal from these mixtures (Published German patent application Ser. No. 2,263,852; Japanese Published patent application Ser. No. 77-045,425) or simply oxidation/incineration of the tar materials to volatile species and collection of the nonvolatile $Rh/Rh_2O_3$ remains (U.S. Pat. No. 3,920,449 and 4,135,911). In the methyl acetate carbonylation process, the catalytically active form of rhodium has been identified as the anion $[Rh(Co)_2I_2]$. This knowledge coupled with the expectation that tar formed in the process will be largely hydrocarbon in nature suggested that aqueous extraction might be a viable technique for the separation of rhodium values from anhydride tar by-products.

While water extracts much of the rhodium present in the tar, the resulting solution is not stable upon heating causing much of the rhodium to be lost from the system through deposits on the process equipment. This instability of the soluble rhodium species is a serious shortcoming of the aqueous extraction technique since the rhodium-containing solution must be concentrated to remove most, e.g., up to 95%, of the water before it is recycled to the carbonylation reactor.

The inclusion of HI in the water used to extract rhodium values from a solution of the above-described tar in a water-immiscible, inert solvent has been found to stabilize the soluble rhodium species, thereby increasing the overall efficiency of the extraction and recycling of the rhodium employed in the carboylation process. Methyl iodide is a particularly suitable solvent since it is used in the carbonylation system. Although the aqueous HI extraction removes most of the rhodium, the tar usually contains some residual rhodium, e.g., up to 10 weight percent or more of the rhodium present in the tar submitted to the aqueous HI extraction. This residual rhodium appears to be bound in some manner to the tar and thus resists extraction by the aqueous HI.

I have discovered that the residual rhodium contained in the tar which has been submitted to an aqueous HI extraction can be recovered by extracting a solution of the tar with aqueous ammonia. The low cost of aqueous ammonia and the feasibility of eliminating it from the anhydride process by stripping renders it a highly advantageous means for recovering the rhodium.

Typically, the tar is removed continuously or intermittently from the carbonylation system in the form of a solution in a mixture of the compounds present in the system. The catalyst-tar solution may be removed either directly from the reactor or, in the case of a system employing a liquid product take-off from the reactor, from some point in the normal catalyst recycle stream. The solution can be submitted to the aqueous HI extraction or can be concentrated by stripping off some of the liquids present. In production facilities in which the rhodium is recycled to the reactor, the tar-containing recycle stream normally will have been concentrated to some extent in the product recovery section of the facilities.

Following the aqueous HI extraction, the organic phase containing the tar and residual rhodium may fed directly to a second extraction unit for extraction with aqueous ammonia. Prior to the aqueous ammonia extraction, the tar solution may be concentrated and, if necessary, diluted with a different water-immiscible, inert solvent, e.g., methylene chloride, chloroform, toluene, methyl isobutyl ketone, etc.

The process in which the tar is formed comprises the preparation of acetic anhydride by the liquid phase carbonylation of methyl acetate in the presence of rhodium and an iodine compound at elevated pressure and temperature wherein a feed mixture containing methyl acetate is continuously fed to a carbonylation reactor and a reaction mixture containing acetic anhydride is continuously removed. Optionally, a catalyst such as a lithium compound can be used and up to about 7 volume percent of the carbon monoxide gas may consist of hydrogen. In the practice of the process, the feed to the reactor is such as to maintain within the reaction mixture (1) about 250 to 1300 ppm, preferably about 500 to 1000 ppm, Rh, (2) about 175 to 5000 ppm, preferably about 1500 to 3700 ppm, lithium and (3) about 7 to 35 weight percent methyl iodide. The remainder of the reactor contents consists mostly of methyl acetate reactant and acetic anhydride product with minor amounts of by-products such as ethylidene diacetate and acetone. The reactor feed optionally may contain a solvent such as acetic acid, e.g., in an amount that will maintain about 5 to 40 weight percent in the reaction mixture. In a liquid take-off system, the catalyst components, e.g., the rhodium, lithium and iodine as methyl iodide, are recovered from the reactor effluent and are recycled. When necessary, fresh rhodium, as rhodium chloride, rhodium acetate or other rhodium containing compound, and lithium, as lithium hydroxide, lithium iodide, lithium acetate or other lithium-containing compound are added to the catalyst recycle. The fresh rhodium and lithium can be conveniently added as a solution in acetic acid. When the iodine needs to be supplemented it may be added to the system as iodine ($I_2$), as methyl iodide or, at least in part, as lithium iodide. In a vapor take-off system, all or essentially all of the rhodium and lithium catalyst components remain in the reactor and thus, the risk of their depletion from the process is reduced considerably. The tar material formed in the process has very reproducible, but poorly resolved spectral features. These features appear in tars formed in both liquid and vapor take-off as well as from runs with both high and low tar formation rates.

From the combined information of IR, H NMR, C NMR, and elemental analysis, certain aspects of the "structure" may be proposed; however, the poor resolution in the H and C NMR spectra thwart hopes for absolute identification and are suggestive of a highly amorphous material. The C NMR shows two major broad band absorptions of approximately equal intensity, one in the alkyl region (13–45$\delta$) and the other in the aromatic region (120–140$\delta$). For the same material, the H NMR shows almost no aromatic protons relative to the alkyl bands at 0.9–1.7 and 1.6–3.0$\delta$. In combination, these two spectra, therefore, suggest a polyalkylated aromatic material substituted to the exclusion of aromatic protons. Additionally, the C shows some very minor absorptions assignable to carbonyl moieties, a feature strongly suggested by the IR band at 1700 cm$^{-1}$. The IR also suggests carbon-oxygen (1180 cm$^{-1}$) and oxygen-hydrogen (36–3300 cm$^{-1}$) bonds. The elemental analysis substantiates the expectations of aromatic unsaturation showing 0.60 unsaturations per carbon and an empirical formula of $C_{36}H_{41}O_4I_{.15}$. Despite the ambiguities of actual tar structure, in a practical sense it is readily soluble in organic solvents and has proven amenable to liquid/liquid extraction.

The amounts of aqueous HI and methyl iodide that can be used to satisfactorily remove the rhodium values from the catalyst-tar solution will vary substantially depending on a number of factors such as the concentration of the tar in the liquids removed from the production system, the amount of rhodium present in the tar and the rhodium extraction efficiency that is desired. The anionic rhodium species that is present in the catalyst-tar solution is soluble in the quantity of methyl iodide that is normally used in the process of this invention. In the presence of water, however, the rhodium is preferentially dissolved in the aqueous phase. Thus, the use of larger amounts of water will result in more of the total rhodium that will be present in the aqueous phase. The use of large amounts of water will also permit optimum phase separation by avoiding emulsion formation.

As stated above, the aqueous phase containing most of the rhodium removed from the acetic anhydride normally should be concentrated to remove most of the water before the rhodium is returned to the process. The purpose for doing so is to minimize the amount of anhydride decomposition that is caused by water which could significantly affect the overall anhydride yield of the process. The use of very large amounts of water therefore can cause an undue amount of energy to be used in the concentration step and thereby increase operating costs disproportionately to the value of the rhodium recovered.

The amount of acetic acid, derived from the acetic anhydride and acid contained in the catalyst-tar solution, in the aqueous phase of the extraction solvent system has, as does the amount of water used, a significant effect on the rhodium distribution coefficient (RDC) defined as [Rh] Methyl Iodide/[Rh] Water. To obtain a RDC of at least about 0.5, preferably at least about 0.25, the concentration of acetic acid in the aqueous phase should not be more than about 8 weight percent and preferably not more than about 4 weight percent. To achieve such an acetic acid concentration while avoiding the use of economically undesirable amounts of water, the catalyst-tar solution is concentrated to a weight of at least 50 percent, preferably to a weight of at least 30% of the catalyst-tar solution removed from the acetic anhydride process. Concentrating the catalyst-tar solution results in a distillate containing methyl iodide, methyl acetate, acetic anhydride and acetic acid which can be combined with the concentrated aqueous phase and recycled to the carbonylation reactor.

The amount of hydrogen iodide required will vary depending on such factors as the amount of lithium acetate present and the temperatures to which the aqueous phase is heated. Normally, sufficient hydrogen iodide is used so that the pH of the aqueous phase is about 1 or less, preferably in the range of about 0.6 to 0.8. The concentration of the HI solution can be varied from concentrated (47%) aqueous HI down to about 6 weight percent. The preferred concentration is about 8 to 10 weight percent. The amount of methyl iodide employed should be at least about 2 parts per weight per part of concentrated catalyst-tar mixture. Methyl iodide ratios of about 3 to 5 (same basis) have been found to give good results.

In the aqueous HI extraction, a portion of the liquid contents containing tar and rhodium, lithium and iodine values is removed intermittently or continuously from the carbonylation system and fed to a hold tank. The tar solution then can be fed periodically to a still-decanter fitted with means for agitation. The composition of the tar solution will vary depending, for example, upon the point from which it is taken from the carbonylation system. Initially, low boiling components such as methyl iodide and methyl acetate along with some acetic acid and acetic anhydride are removed to give a concentrated solution of the tar and rhodium catalyst in acetic anhydride and acetic acid. Methyl iodide and the aqueous hydrogen iodide are added to the concentrated solution with agitation. Best results are obtained if the methyl iodide is added first to the concentrated solution which has been cooled to just below the boiling point of methyl iodide. After partitioning, agitation is stopped, the aqueous and organic layers are allowed to separate and the methyl iodide phase containing the tar is removed from the bottom of the still-decanter. The remaining aqueous solution of hydrogen iodide and rhodium, lithium and iodine values in water and acetic acid is vacuum distilled to remove most of the water, e.g., 90%. The remaining catalyst solution can then be combined with the liquids initially removed and recycled to the carbonylation reactor.

The process may be modified to provide for continuous operation by feeding catalyst-tar solution, aqueous hydrogen iodide and methyl iodide simultaneously to a mix tank and feeding the mixture to about the midpoint of an extraction column. An aqueous stream containing most of the catalyst values is removed from the top of the column and the methyl iodide containing the tar is removed from the bottom. Normally, additional aqueous hydrogen iodide and methyl iodide are added to the lower and upper portions, respectively, of the extraction column.

The aqueous ammonia extraction can be carried out using either of the above-described techniques using the solution of the rhodium-containing tar obtained from the above processes or a solution of the tar in another water-immiscible, inert solvent. The volumes of the water-immiscible solvent and aqueous ammonia used in the extraction can be varied substantially depending on various factors such as the equipment used, whether the process is a batch or continuous one, etc. To maximize the amount of rhodium recovered while minimizing the amount of water it is preferred that concentrated aqueous ammonia, i.e., a 30 weight percent solution, be used.

The temperature at which the process of the present invention is carried out is not important and can be varied substantially depending on a number of factors such as the vessels used, the particular water-immiscible, inert solvent employed, etc. The combined use of high temperatures and methyl iodide may result in the reaction of the methyl iodide and ammonia to some extent.

The rhodium contained in the aqueous ammonia-rhodium extract obtained from my novel process may be returned to the carbonylation reactor as a solution in acetic acid resulting from the addition to the extract of sufficient acetic anhydride to consume the water. In a carbonylation process which involves a continuous catalyst recycle stream containing acetic anhydride, the extract can be continuously fed to the recycle stream. Alternatively, the extract can be stripped dry, the resulting rhodium solids slurried with methyl iodide and the slurry fed directly to the reactor or to the catalyst recycle stream.

The practice of the process is further illustrated by the following examples. The tar employed in the examples resulted from a carbonylation system comprising a 3.5 liter reactor consisting of five feet five inches of two-inch Sch. 40 pipe. A gas mixture of carbon monoxide and 5 volume percent hydrogen is fed through a gas sparger at the bottom of the reactor. Through a reactor feed line, located above the sparger, is fed a mixture containing methyl acetate, acetic acid, acetic anhydride, methyl iodide, lithium and rhodium at an average rate of about 12,600 grams/hour. The composition of the feed stream normally is 18–20% methyl iodide, 55–40% methyl acetate, 15–20% acetic acid, 15–20% acetic anhydride, about 750 ppm rhodium and about 3500 ppm lithium. Using this sytem acetic anhydride is produced at about 750 psig and 190° C. at a space time yield of about 600 grams/liter-hour. The reactor contents overflow from the top of the reactor to a reactor separator pot where some of the unreacted carbon monoxide and other gases are separated from the liquid and purged from the system. The liquid from the reactor separator pot passes through a valve which reduces the pressure from about 750 psig to 10–20 psig. The liquid passes through a flash evaporator, wherein about 80–90% of the material is vaporized and enters an evaporator separator pot (about 1 psig) wherein the vapor and liquid are separated. The liquid, which consists mainly of acetic acid and acetic anhydride in which the rhodium and lithium catalyst components are dissolved along with minor amounts of methyl iodide and methyl acetate, is recycled to the reactor. The vapors from the evaporator separator pot are fed to a column in which the temperature is maintained at about 140° C. at the base and about 100° C. at the top. Crude acetic anhydride suitable for further refining is removed from the lower portion of the column. The low boilers (methyl acetate, methyl iodiode and some acetic acid) are taken overhead and fed to a low boiler blend tank to which makeup methyl acetate is also fed. The contents of the blend tank are continuously fed to the reactor feed line. A tar solution obtained from the above-described catalyst recycle stream was submitted to an aqueous HI extraction, the methyl iodide was stripped off and the rhodium-containing tar was used in the following examples. The aqueous HI extraction is described in detail in co-pending U.S. application Ser. No. 304,773, filed Sept. 23, 1981, the disclosure of which is incorporated herein.

The invention will be further illustrated by the following examples although it will be understood that these examples are included merely for purposes of illustration and are not intended to limit the scope of the invention.

EXAMPLE 1

An approximately 50% methylene chloride solution of the tar (syrupy liquid, d=1.323) was utilized in these experiments. This solution contained approximately 400 parts per million (ppm) residual rhodium. Portions (25 ml) of this sample were subjected to extraction in a 125 ml separatory funnel with equal volumes of concentrated aqueous ammonia (28.8%). Extraction was achieved by shaking the funnel vigorously for 30 seconds and allowing the layers to separate for 10 minutes. Organic and aqueous phases were analyzed by atomic absorption spectrophotometry and the extraction efficiency calculated. Approximately 90% of the residual rhodium was removed from the organic layer with one extraction and 88% of the remainder was removed with a second extraction for a total of $\geq 98\%$ recovery. Extractions with lower ammonia concentrations (~8%) proved to be somewhat less effective in removing residual rhodium than concentrated ammonia, removing about 70% with one extraction.

EXAMPLE 2

A 25 ml portion of this same methylene chloride solution was stripped to dryness at 55° C. and 5 mm pressure. The residue, approximately 10 g., was redissolved in 25 ml of methyl iodide. Subsequent extraction with 25 ml of concentrated aqueous ammonia using the technique described in Example 1 yielded 80% of the rhodium in the aqueous phase with one extraction.

The invention has been described in detail with particular reference to preferred embodiments thereof, but it will be understood that variations and modifications can be effected within the spirit and scope of the invention.

I claim:

1. Process for the recovery of residual rhodium from tar obtained by submitting a catalyst-tar solution to an extraction using methyl iodide and aqueous hydrogen iodide, thereby recovering catalyst values in the aqueous phase and tar containing residual rhodium in the methyl iodide phase wherein the catalyst-tar solution is derived from a production system in which acetic anhydride is prepared by carbonylating methyl acetate in the presence of rhodium, lithium and methyl iodide wherein the residual rhodium-containing tar is submitted to an extraction using a water-immiscible, inert solvent for the tar and aqueous ammonia and recovering residual rhodium in the aqueous phase.

* * * * *